US008186999B2

(12) United States Patent
Andersson et al.

(10) Patent No.: US 8,186,999 B2
(45) Date of Patent: May 29, 2012

(54) SYSTEM AND ARRANGEMENT FOR PRODUCTION AND INSERTION OF A DENTAL BRIDGE STRUCTURE

(75) Inventors: Matts Andersson, Lerum (SE); Izidor Brajnovic, Gothenburg (SE); Andreas Pettersson, Gothenburg (SE)

(73) Assignee: Nobel Biocare Services AG (CH)

( * ) Notice: Subject to any disclaimer, the term of this patent is extended or adjusted under 35 U.S.C. 154(b) by 303 days.

(21) Appl. No.: 12/572,169

(22) Filed: Oct. 1, 2009

(65) Prior Publication Data

US 2010/0028827 A1 Feb. 4, 2010

Related U.S. Application Data

(62) Division of application No. 10/582,417, filed as application No. PCT/SE2004/001527 on Oct. 22, 2004, now abandoned.

(30) Foreign Application Priority Data

Dec. 10, 2003 (SE) ...................................... 0303309

(51) Int. Cl.
*A61C 19/04* (2006.01)
*A61C 9/00* (2006.01)
(52) U.S. Cl. .......................................... 433/72; 433/214
(58) Field of Classification Search .................... 433/72, 433/75, 76, 172–176, 214–215; 434/263, 434/270; 623/11.11, 901
See application file for complete search history.

(56) References Cited

U.S. PATENT DOCUMENTS

| 4,470,815 | A |   | 9/1984  | Hazar          |        |
| 4,850,870 | A |   | 7/1989  | Lazzara et al. |        |
| 4,906,420 | A |   | 3/1990  | Brajnovic et al. |      |
| 4,998,881 | A |   | 3/1991  | Lauks          |        |
| 5,030,096 | A |   | 7/1991  | Hurson et al.  |        |
| 5,062,800 | A |   | 11/1991 | Niznick        |        |
| 5,320,529 | A | * | 6/1994  | Pompa          | 433/76 |

(Continued)

FOREIGN PATENT DOCUMENTS

DE 601 26 120 11/2007

(Continued)

OTHER PUBLICATIONS

U.S. Appl. No. 11/172,354, filed Jun. 30, 2005, Brajnovic et al., Device Forming Part of a Dental Screwing Arrangement.

(Continued)

*Primary Examiner* — Todd Manahan
*Assistant Examiner* — Matthew Nelson
(74) *Attorney, Agent, or Firm* — Knobbe Martens Olson & Bear LLP

(57) ABSTRACT

A system comprises a computer appliance designed to receive, and to present on screen, first information transmitted from identification equipment and based on detection of a jaw bone structure. Modification information which can be introduced into the computer appliance shows a visual dental bridge structure applied on the jaw bone structure with associated teeth and dentine. Orientations for implants are also shown. The computer appliance produces a CAD file which is based on the first information and the modification information. The file is received in a stereolithography machine which issues second information which can be processed in the equipment for production of the physical template which includes through-bores for sleeves which define implant orientation. A working model is produced with the aid of the physical template. The invention also relates to an arrangement of a template produced by stereolithography and by means of information from the computer appliance.

11 Claims, 4 Drawing Sheets

U.S. PATENT DOCUMENTS

| | | | |
|---|---|---|---|
| 5,482,463 | A | 1/1996 | Wilson et al. |
| 5,605,457 | A | 2/1997 | Bailey et al. |
| 5,605,458 | A | 2/1997 | Bailey et al. |
| 5,607,304 | A | 3/1997 | Bailey et al. |
| 5,681,167 | A | 10/1997 | Lazarof |
| 5,718,579 | A * | 2/1998 | Kennedy .................. 433/75 |
| 5,725,376 | A | 3/1998 | Poirier |
| 5,743,916 | A | 4/1998 | Greenberg et al. |
| 5,768,134 | A | 6/1998 | Swaelens et al. |
| 5,851,115 | A | 12/1998 | Carlsson et al. |
| 5,876,204 | A | 3/1999 | Day et al. |
| 5,934,906 | A * | 8/1999 | Phimmasone ............... 433/172 |
| 5,967,305 | A | 10/1999 | Blonder et al. |
| 5,967,777 | A | 10/1999 | Klein et al. |
| 5,989,028 | A | 11/1999 | Niznick |
| 6,099,311 | A | 8/2000 | Wagner et al. |
| 6,159,008 | A | 12/2000 | Kumar |
| 6,174,166 | B1 | 1/2001 | Jörneus |
| 6,217,332 | B1 | 4/2001 | Kumar |
| 6,227,861 | B1 | 5/2001 | Cartledge et al. |
| 6,254,639 | B1 * | 7/2001 | Peckitt ...................... 623/11.11 |
| 6,287,117 | B1 | 9/2001 | Niznick |
| 6,287,119 | B1 | 9/2001 | Van Nifterick et al. |
| 6,305,939 | B1 | 10/2001 | Dawood |
| 6,312,260 | B1 | 11/2001 | Kumar et al. |
| 6,315,562 | B1 | 11/2001 | Kumar |
| 6,319,000 | B1 | 11/2001 | Branemark |
| 6,382,975 | B1 | 5/2002 | Poirier |
| 6,561,805 | B2 | 5/2003 | Kumar |
| 6,619,958 | B2 | 9/2003 | Beaty et al. |
| 6,626,911 | B1 | 9/2003 | Engman et al. |
| 6,672,870 | B2 | 1/2004 | Knapp |
| 6,692,254 | B1 | 2/2004 | Kligerman et al. |
| 6,705,863 | B2 | 3/2004 | Phan et al. |
| 6,788,986 | B1 * | 9/2004 | Traber et al. ................ 700/98 |
| 6,793,491 | B2 | 9/2004 | Klein et al. |
| 6,814,575 | B2 | 11/2004 | Poirier |
| 6,997,707 | B2 | 2/2006 | Germanier |
| 7,175,435 | B2 | 2/2007 | Andersson et al. |
| 7,236,842 | B2 * | 6/2007 | Kopelman et al. .............. 700/98 |
| 7,331,786 | B2 | 2/2008 | Poirier |
| 7,950,924 | B2 | 5/2011 | Brajnovic |
| 2001/0053510 | A1 | 12/2001 | Ranalli |
| 2002/0064759 | A1 | 5/2002 | Durbin et al. |
| 2002/0102517 | A1 * | 8/2002 | Poirier ...................... 433/173 |
| 2002/0177104 | A1 | 11/2002 | Klein et al. |
| 2003/0186187 | A1 | 10/2003 | Germanier |
| 2004/0137408 | A1 * | 7/2004 | Embert et al. .............. 433/201.1 |
| 2004/0158342 | A1 * | 8/2004 | Wolf et al. ...................... 700/98 |
| 2004/0254667 | A1 * | 12/2004 | Ganley et al. .................. 700/117 |
| 2004/0259051 | A1 | 12/2004 | Brajnovic et al. |
| 2005/0170311 | A1 | 8/2005 | Tardieu et al. |
| 2006/0008763 | A1 | 1/2006 | Brajnovic et al. |
| 2006/0008770 | A1 | 1/2006 | Brajnovic et al. |
| 2007/0281270 | A1 | 12/2007 | Brajnovic |
| 2008/0118895 | A1 | 5/2008 | Brajnovic |
| 2008/0153065 | A1 | 6/2008 | Brajnovic et al. |

FOREIGN PATENT DOCUMENTS

| | | | |
|---|---|---|---|
| EP | 0689804 | A1 | 1/1996 |
| EP | 1205159 | | 5/2002 |
| EP | 1317910 | A1 | 6/2003 |
| EP | 1364625 | A1 | 11/2003 |
| FR | 2836372 | A1 | 8/2003 |
| GB | 1131948 | | 10/1968 |
| JP | 2001-59113 | | 4/1989 |
| JP | 2004 521671 | | 7/2004 |
| SE | 457691 | | 1/1989 |
| SE | 508662 | C2 | 10/1998 |
| SE | 522958 | | 3/2004 |
| WO | WO 94/14388 | A1 | 7/1994 |
| WO | WO 96/37163 | A1 | 11/1996 |
| WO | WO 97/49351 | | 12/1997 |
| WO | WO 98/44865 | A1 | 10/1998 |
| WO | WO 00/27300 | | 5/2000 |
| WO | WO 00/28914 | | 5/2000 |
| WO | WO 01/54609 | | 8/2001 |
| WO | WO 01/58379 | A1 | 8/2001 |
| WO | WO 02/38074 | | 5/2002 |
| WO | WO 02/053055 | A1 | 7/2002 |
| WO | WO 02/053056 | A1 | 7/2002 |
| WO | WO 02/053057 | A1 | 7/2002 |

OTHER PUBLICATIONS

U.S. Appl. No. 12/014,031, filed Jan. 14, 2008, Brajnovic et al., Device Forming Part of a Dental Screwing Arrangement.

U.S. Appl. No. 11/172,291, filed Jun. 30, 2005, Brajnovic, Izidor, Device and Arrangement for Fixture Installation.

U.S. Appl. No. 12/419,876, filed Apr. 7, 2009, Brajnovic, Izidor, Device and Arrangement for Fixture Installation.

U.S. Appl. No. 10/582,417, filed May 23, 2007, Andersson et al., System and Arrangement for Production and Insertion of a Dental Bridge Structure.

U.S. Appl. No. 12/572,169, filed Oct. 1, 2009, Andersson et al., System and Arrangement for Production and Insertion of a Dental Bridge Structure.

U.S. Appl. No. 12/548,328, filed Aug. 26, 2009, Brajnovic, Izidor, Arrangement and Device for Using a Template to Form Holes for Implants in Bone, Preferably Jaw Bone.

U.S. Appl. No. 12/299,598, filed Jun. 1, 2009, Brajnovic, Izidor, Device for Securing a Dental Implant in Bone Tissue, a Method for Making a Surgical Template and a Method of Securing a Dental Implant in Bone Tissue.

U.S. Appl. No. 12/371,545, filed Feb. 13, 2009, Andersson et al., Method, Arrangement and Program for a Prosthetic Installation.

U.S. Appl. No. 12/522,706, filed Sep. 28, 2010, Pettersson, Andreas, Method and System for Dental Planning and Production.

International Preliminary Report on Patentability and Written Opinion for Application No. PCT/SE 2001/002898 (the counterpart of U.S. Appl. No. 10/451,535 completed on Dec. 9, 2002 in 5 pages.

International Preliminary Report on Patentability and Written Opinion for Application No. PCT/SE 2003/001975 (the PCT counterpart of U.S. Appl. No. 11/172,291) mailed on Feb. 2, 2005 in 4 pages.

International Preliminary Report on Patentability and Written Opinion for Application No. PCT/SE 2004/001527 (the PCT counterpart of co-pending U.S. Appl. No. 10/582,417) mailed on Jan. 21, 2005 in 7 pages.

International Preliminary Report on Patentability and Written Opinion for Application No. PCT/SE 2005/001074 (the PCT counterpart of co-pending U.S. Appl. No. 11/573,193) mailed Nov. 2, 2005 in 7 pages.

International Preliminary Report on Patentability and Written Opinion for Application No. PCT/SE 2005/001075 (the counterpart of the co-pending U.S. Appl. No. 11/573,196) mailed Nov. 2, 2005 in 7 pages.

International Preliminary Report on Patentability and Written Opinion for Application No. PCT/SE 2007/000431 (the counterpart of U.S. Appl. No. 12/299,598) mailed on Apr. 9, 2007 in 13 pages.

International Preliminary Report on Patentability for Application No. PCT/SE 2002/02393 (the PCT counterpart of co-pending U.S. Appl. No. 10/710,170) completed on Mar. 8, 2004 in 3 pages.

International Search Report for Application No. PCT/SE 2001/002898 (the counterpart of the U.S. Appl. No. 10/451,535 mailed Nov. 4, 2002 in 4 pages.

International Search Report for Application No. PCT/SE 2002/02393 (the PCT counterpart of co-pending U.S. Appl. No. 10/710,170) mailed Mar. 20, 2003 in 2 pages.

International Search Report for Application No. PCT/SE 2003/001975 (the PCT counterpart of U.S. Appl. No. 11/172,291) completed on Feb. 24, 2004 in 3 pages.

International Search Report for Application No. PCT/SE 2003/001976 (the PCT counterpart of abandoned U.S. Appl. No. 11/172,354 and co-pending U.S. Appl. No. 12/014,031) mailed Mar. 11, 2004 in 2 pages.

International Search Report for Application No. PCT/SE 2004/001527 (the PCT counterpart of co-pending U.S. Appl. No. 10/582,417) mailed Jan. 21, 2005 in 3 pages.

International Search Report for Application No. PCT/SE 2005/001074 (the PCT counterpart of co-pending U.S. Appl. No. 11/573,193) mailed Nov. 2, 2005 in 3 pages.

International Search Report for Application No. PCT/SE 2005/001075 (the counterpart of the co-pending U.S. Appl. No. 11/573,196).

International Search Report for Application No. PCT/SE 2007/000431 (the counterpart of U.S. Appl. No. 12/299,598) mailed Apr. 9, 2007 in 4 pages.

European Patent Office Communication Pursuant to Rule 114(2) EPC with Third Party Observation Letter mailed Mar. 6, 2009 in 4 pages, received in corresponding EP Application No. 02793696.2 (EP counterpart of 290C1).

Gateno et al., A New Technique for the Creation of a Computerized Composite Skull Model, J Oral Maxillofac Surg, 2003, vol. 61, pp. 222-227.

Tardieu P.: "Computer assistance in the planning and implementation of implant treatments. The Materialise concept and the SurgiCase Programme." WWW.DENTALESPACE.COM 2000, pp. 1-11.

Tardieu P.B. and B. Philippe: "Total maxillary edentation with terminal osseus atrophy therapeutic treatment" IMPLANT vol. 7, No. 3, 2000, pp. 199-210.

Tardieu, Philippe B.: "Aide Informatique Aux Diagnostics Et Aux Traitement Implantaires. Guides Chirurgico-Scannographiques. Programme Simm:Plan", believed to be published in 1999, pp. 1-27.

* cited by examiner

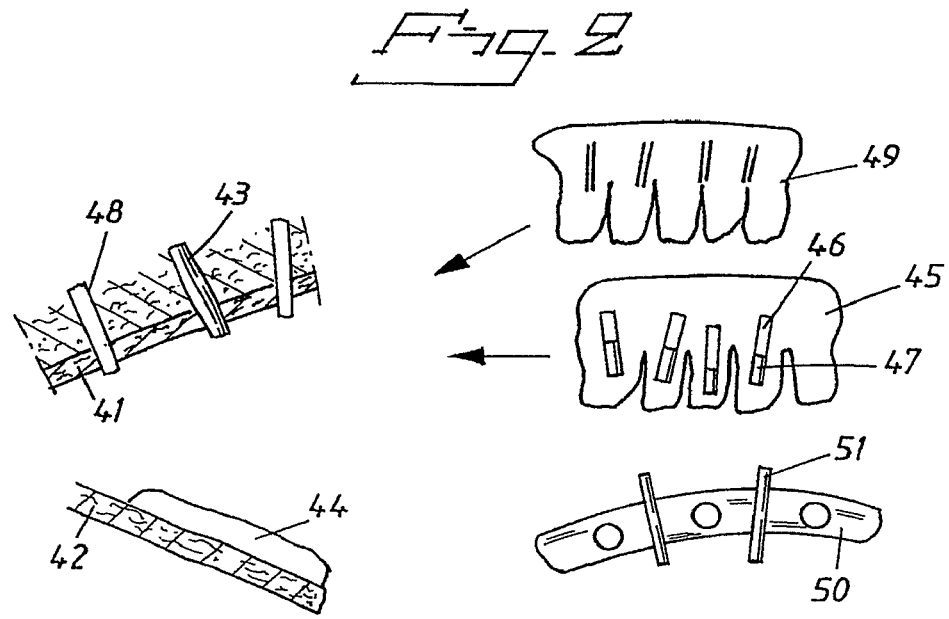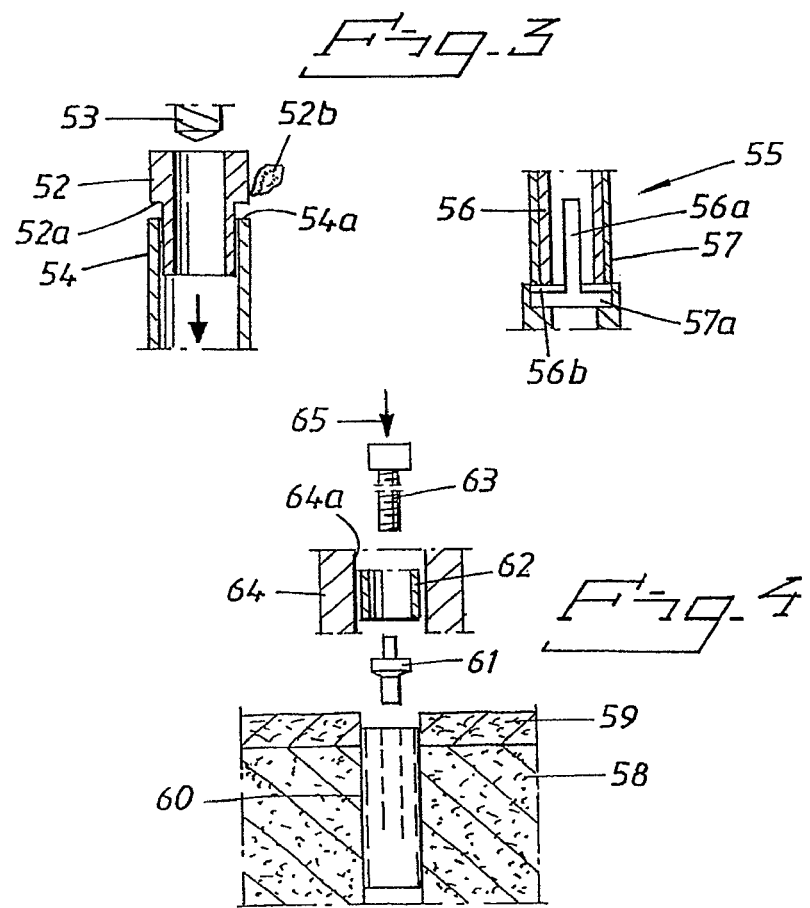

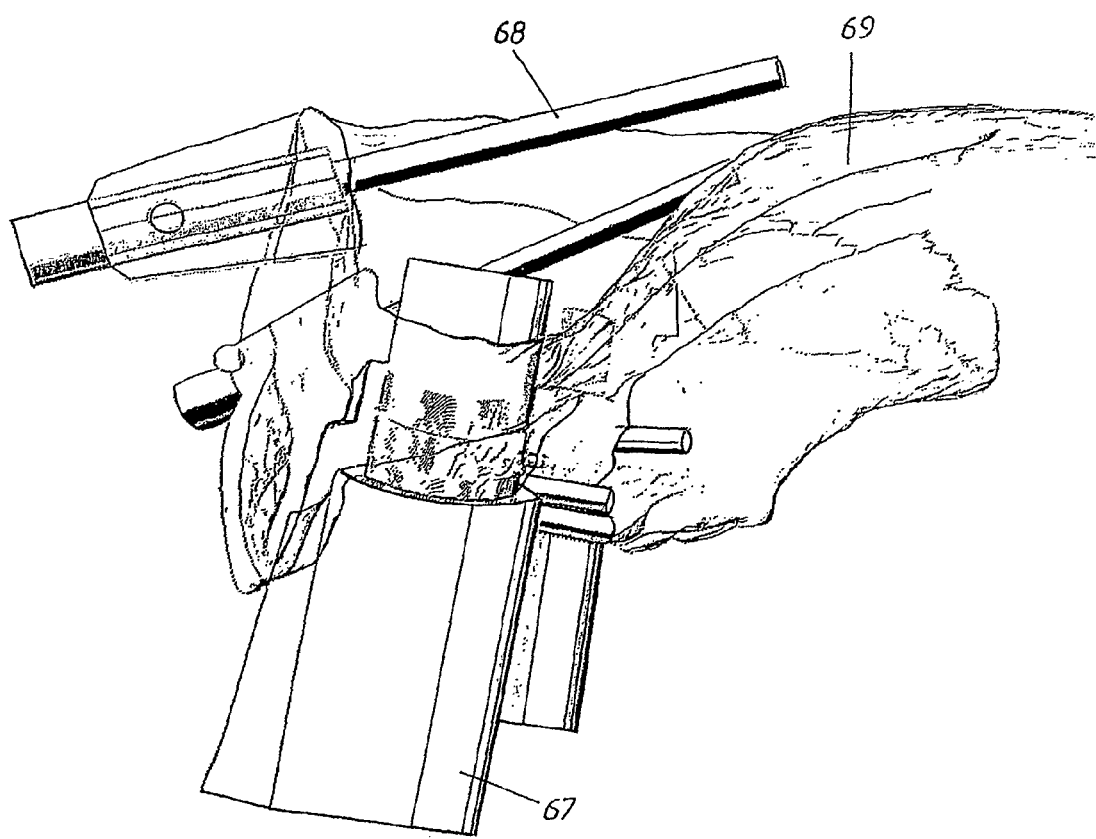

SYSTEM AND ARRANGEMENT FOR PRODUCTION AND INSERTION OF A DENTAL BRIDGE STRUCTURE

CROSS-REFERENCE TO RELATED APPLICATIONS

This application is a divisional of U.S. application Ser. No. 10/582,417, which is the U.S. National Phase under 35 U.S.C. §371 of International Application No. PCT/SE04/01527, filed Oct. 22, 2004, which claims priority under 35 U.S.C. §119 to Swedish Patent Application No. SE 0303309-9, filed Dec. 10, 2003, the disclosures of which are incorporated in their entirety by reference herein.

BACKGROUND OF THE INVENTION

The following disclosure relates inter alia to a system for production and insertion of a real dental bridge structure in a real jaw bone structure by means of a number of successive steps performed using equipment belonging to one or more parties.

SUMMARY

In certain embodiments, the equipment comprises identification equipment, a computer appliance, stereolithography equipment, equipment for production of a physical template, equipment for production of a working model in cooperation with an articulator, equipment for production of the dental bridge structure and insertion equipment for fitting the dental bridge structure on the implant in the jaw bone structure. Jaw bone structure can relate, for example, to the structure of the upper jaw or lower jaw. The disclosure also relates to a template produced by stereolithography and from information from the computer appliance and used for producing, on the one hand, a dental bridge structure that can be applied on an implant in the jaw bone structure, and, on the other hand, for guiding of hole-forming means, for example a drill, for forming holes for the implants. Generally similar systems may be found in patent application no. SE 0004884-3.

Previous templates are described in patent application nos. SE 0004885-0, SE 0004886-8, SE 0104431-2, SE 0104432-0, SE 0203898-2, SE 0203899-0 and SE 0203900-6.

There is a need for reducing the time and cost associated with making and/or using dental templates. Thus, for example, the production of the template may be reduced by 30-50% and, among other advantages, the stereolithography be reduced. Embodiments described herein allow for relatively high precision while reducing the time and cost associated with production.

In accordance with the disclosure, some or all of the production steps or functions may be performed by parties already operating on the market. The parties may cooperate with one another, the number of parties may be able to vary and the production steps may be divided into testing, insertion and handling, production by means of STL (sterolithography technology) and model production, and production by the dental technician. For support and possible production of one or more of the functions, other parties may be involved. Such parties may include parties who provide a generally fully automatic production system for dental products such as the PROCERA® type.

A system according to embodiments of the disclosure is a computer appliance designed to receive, and present on screen, first information transmitted from a identification equipment and based on detection of a jaw bone structure. The computer appliance can be arranged with operating elements which may be used to modification information concerning, on the one hand, a visual dental bridge structure applied on the visual jaw bone structure with associated teeth and dentine. The computer appliance may further be used to modify orientations of the implants in the visual dental bridge structure and visual jaw bone structure. Moreover, the computer appliance is arranged to generate or to cause generation of a CAD file based on the first information and the modification information and to transmit the CAD file to the stereolithography machine. Second information can be processed using the equipment for production of a physical template which includes through-bores for sleeves arranged to determine the recessed positions and longitudinal directions for one or more implants. The physical template can on the one hand form the basis for production of a working model and, on the other hand, serve as template for forming holes in the jawbone defined with the sleeves using insertion equipment (e.g., drill).

In some embodiment, the identification and computer appliances can be assigned to a first party consisting of a party treating a patient, such as, for example a surgeon or dentist. The stereolithography machine can be assigned to a second party. The equipment for production of the template, working model and real dental bridge structure can be assigned to a third party, for example a dental technician. A fourth party with equipment of a higher order can also be involved. The fourth party can ensure, for example, the provision of information and/or handling or production of one or more of said functions or parts thereof. In certain embodiments, the stereolithography machine can be accessed by any of said parties.

An arrangement according to the disclosure includes a template and dental bridge structure provided with through-holes, the through-holes provided with sleeves. The sleeves can define, for example, the degree to which the implants are recessed and their orientation.

In further embodiments, the sleeves are designed to achieve a degree or amount of recessing in the template. In one embodiment, the sleeves can be anchored to the template with dental cement. In a preferred embodiment, the template is arranged to reproduce or comprise a material or part which corresponds to the dentine or gum replacement over those parts which extend over the portions of jaw bone the dental bridge is intended to extend over. In some embodiments, the template is produced in said machine from plastic material with a very low coefficient of shrinkage.

In some embodiments, after fixture planning, planning files can be converted to CAD files and SLA models (rapid prototyping) can be ordered in so-called STL technology. Part of the model can simulate the patient's upper jaw or lower jaw, while another part simulates the patient's dental prosthesis. Thereafter, the working model is produced at the dental laboratory. The template can be planned on a computer using CAD and includes data or information which can be used to order a template produced by STL technology. The template can include sleeves for guiding the drill, implant and anchoring pins. The sleeves can be cemented in place with dental cement.

The template can be used as an impression for producing a working model (e.g., in plaster), which can be mounted in an articulator (e.g., with the aid of a bite index against the dental model of the opposite jaw/jaw bone). The dental bridge can be produced on the working model. The template can also form the gum replacement over the implant in the jaw bone and around spacers in connection with production of the working model.

Embodiments of systems and methods according to the embodiments of the disclosure will be described below with reference to the attached drawings.

BRIEF DESCRIPTION OF THE DRAWINGS

FIG. 2 shows upper and lower jaws of a patient, a bridge and a template according to embodiments described herein.

FIG. 3 shows, in vertical cross-section, two different embodiments of sleeves used in the template according to embodiments described herein.

FIG. 4 shows, in vertical cross-section, application of a sleeve in relation to an implant, and a fastening screw for the sleeve and the implant according to embodiments described herein.

FIG. 7 shows a perspective view, from the side, of implants and anchoring pins in an upper jaw according to embodiments described herein.

DETAILED DESCRIPTION OF THE PREFERRED EMBODIMENT

A template can be planned using a computer (e.g., using a CAD tool) by modifying the scanned patient prosthesis. In this way, it is possible to avoid the problem of having to produce the template at a dental laboratory. This is an advantage since the template there is made of acrylic or of a plastic which has a certain shrinkage tendency, with deterioration of the precision as a consequence. According to the disclosure, the template can be mounted in the articulator with the aid of a bite index. In this way, it is possible to record the bite relationships of the jaws. The template is used by the surgeon to place the implant at a planned site in the patient's mouth. Anchoring pins which are inserted from the side of the template between the planned implants may be included. In this way, the template is held in place in the mouth with the aid of a bite index which is produced by the dental technician in the articulator. This solves the problem of obtaining the correct bite relationship between the dental bridge and the opposite jaw after the operation. The template includes data for planning, so that it is generally not necessary to produce the bone part of the patient's jaw. This reduces the production time and costs associated with using the stereolithography machine. Error placing the prosthesis model in the correct relationship to the bone part is reduced.

Figure 1:
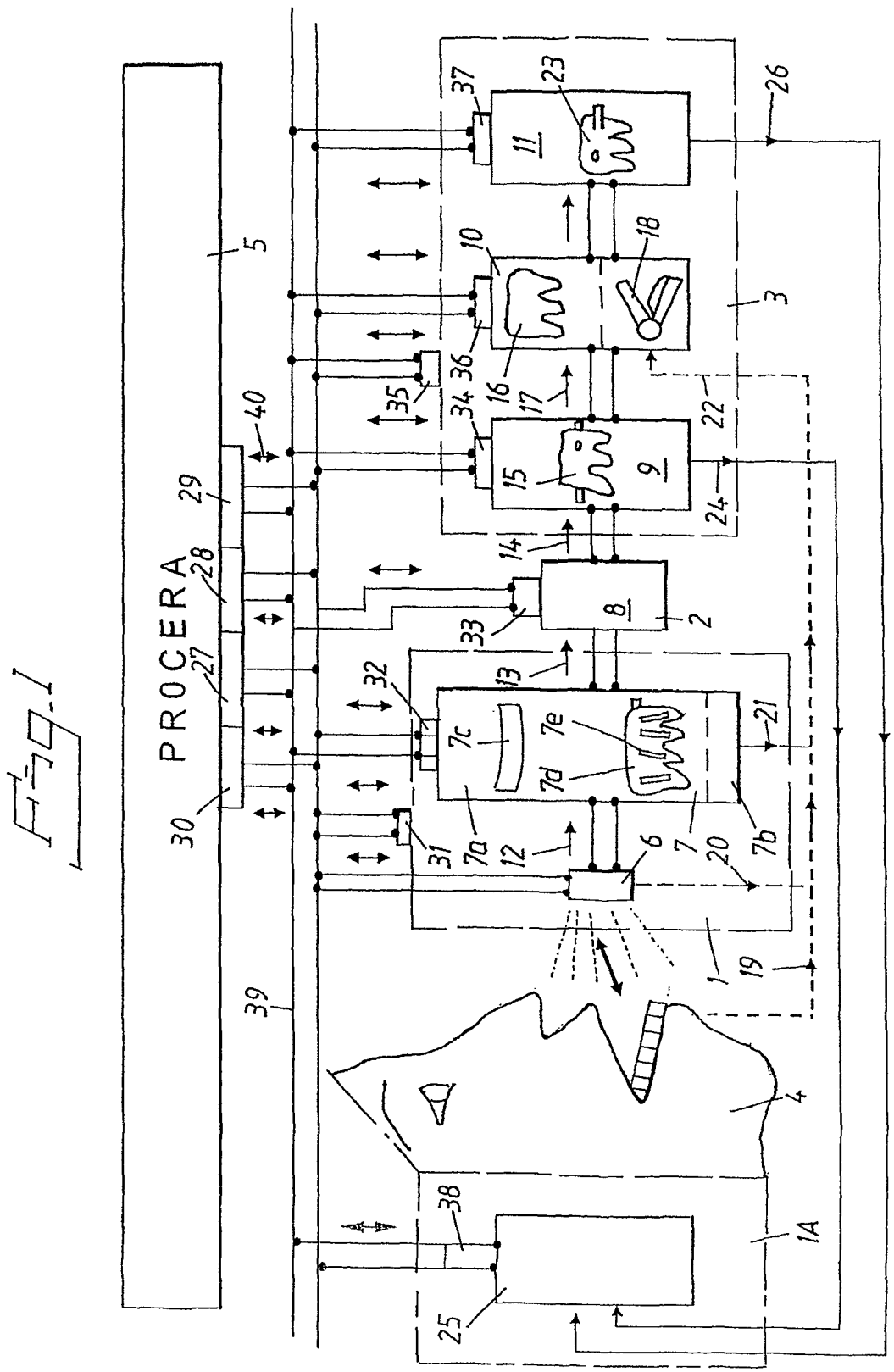
FIG. 1 shows, in block diagram form, example equipment and parties involved according to embodiments described herein.

In FIG. 1, a first party is indicated symbolically by 1, a second party by 2, and a third party by 3. The first party can be a surgeon, dentist, etc., who is to test and fit a dental bridge on a patient 4. The second party can be an owner of a stereolithography machine. The third party can be a dental technician. FIG. 1 also indicates a fourth party represented by a generally automatic production system for dental products; in the illustrative embodiment the party 5 is designated as PROCERA®. The first party may have access to identification equipment 6. In addition, the first party has access to a computer appliance 7. The stereolithography machine is symbolized by 8. The dental technician has access to equipment for production of a physical template 9, and equipment 10 for production of a working model in cooperation with an articulator function. In addition, the dental technician produces the final dental bridge using equipment 11.

The identification equipment 6 may include conventional identification equipment. Thus, for example, the party 1 can produce an impression using conventional means. Alternatively, cameras, laser equipment, etc., can be used. The computer appliance 7 comprises, a computer screen 7a and an operating element 7b which can consist of a keyboard, voice communication unit, etc. Depending on the identification, the relevant jaw/jaw bone, in this case upper jaw, of the patient 4 can be indicated. The upper jaw structure is symbolized by 7c. In addition, the first party can modify the computer model of the jaw bone structure on the screen and build up a dental crown structure applied on the jaw bone. Such a structure is indicated by 7d. For the sake of clarity, the upper jaw 7c and the complete structure 7d have been shown as two simultaneous representations. Said representations can of course be indicated one at a time. In the representation 7d, the orientations for the implants and their directions are shown by 7e. The computer appliance can operate with conventional programs (CAD programs) and file management systems.

The scanning equipment 6 of certain embodiments can provide the computer appliance with first information 12 which represents the scanned jaw bone structure. This is exported to the computer appliance. In turn, the computer appliance generates a CAD file which is represented by 13 in FIG. 1. The CAD file is received by the stereolithography machine which sets the conditions for a physical model transferred to the dental technician 9 for application of sleeves, inter alia. This transfer is represented by 14. The physical model is shown by 15. The dental technician uses the model 15 for production of a working model 16, and the transfer function between the units 9 and 10 is symbolized by 17. The production of the working model takes place in conjunction with an articulator function which is represented by 18. The bite index for the articulator function can be transferred from the patient 4, the computer appliance 7 and/or the identification equipment 6. Said transfers are represented by 19, 20 and 21. The bite index transfer to the articulator function has been symbolized by 22.

The real dental bridge 23 is produced in the equipment 11 by the party 3. From the equipment 9, the physical template 15 can be transferred to the surgeon or equivalent. This transfer is represented by 24. The party 1 can also have access to equipment symbolized by 1A. This equipment can include drilling equipment and insertion equipment for fitting the template and dental bridge on the patient 4. The finished dental bridge can be transferred to the first party, as has been represented by the transfer arrow 26. Formation of holes in the patient's jaw bone with the aid of the template and insertion of the finished dental bridge can take place in a manner known per se and will therefore not be described in detail here.

In accordance with FIG. 1, the fourth party 5 can provide a support function or production of one or more of said function steps. This is shown in the figure where the automatic system comprises adaptation units 27, 28, 29 and 30. The equipment of the other parties can also be connected via adaptation units 31, 32, 33, 34, 35, 36, 37 and 38. The transfers can take place via general communication means 39, for example the telecommunications network, Internet, computer network, etc. The transfer functions are represented by bi-directional arrows, indicating two-way communications. The arrows are represented by 40.

In FIG. 2, an upper jaw of a patient is indicated by 41 and a lower jaw by 42. In the upper jaw, the party 1 has inserted implants 43 in which a dental bridge is to be secured. A set of teeth in the patient's lower jaw is indicated by 44 and, in accordance with embodiments described herein, the bite relationship between the dental bridge to be implanted and the teeth of the lower jaw can be implemented and/or determined with the aid of a bite index. Reference number 45 indicates a template in accordance with the above. The template comprises recesses 46 for sleeves 47. The sleeves can be used as guide members for formation of holes 48 into which the implants 43 can be screwed or recessed. Reference number 49 indicates the finished dental bridge structure to be anchored on the implants 43 in the upper jaw. The upper jaw is also shown diagrammatically from underneath by reference number 50 in order to indicate orientations for anchoring pins 51 which may extend substantially in a horizontal plane in the jaw structure. FIG. 3 shows a first embodiment of a sleeve 52 which is used for guiding a drill 53 for forming the implant hole 48. The sleeve has a stop edge 52a which can cooperate with the template 54 via a stop surface 54a on the latter. FIG. 3 also shows a second embodiment 55 of a sleeve 56 which is provided with slits 56a. The template 57 in this case has an internal recess 57a into which a snap-fit flange 56b on the sleeve can snap when the sleeve assumes its final position in the template 57. A click noise may sound upon snap-fitting of the flange 56b into the recess 57.

FIG. 4 shows an implant 60 applied in a jaw bone and dentine 59. The implant can cooperate with an attachment part 61 over which a sleeve 62 in accordance with the above can be engaged. The components can be held together with a retaining screw 63. The sleeve 62 may be mounted in the template or dental bridge part which is indicated by 64. The parts are shown in the disassembled state for the sake of clarity. The parts can be joined together in the direction of the arrow 65. A through-hole in the template 64 is shown by 64a. Cement which is used for securing the sleeve to the template is shown symbolically by 52b.

Figure 5:
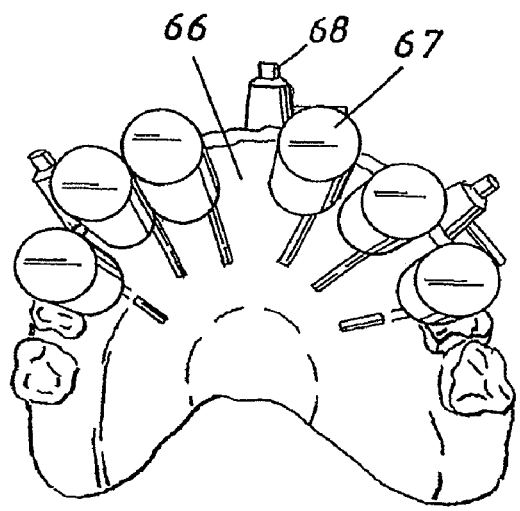
FIG. 5 shows, from underneath, a model of an upper jaw in which implants are applied with associated anchoring tubes and anchoring pins which extend horizontally in the dentine between the implants according to embodiments described herein.
Figure 6:
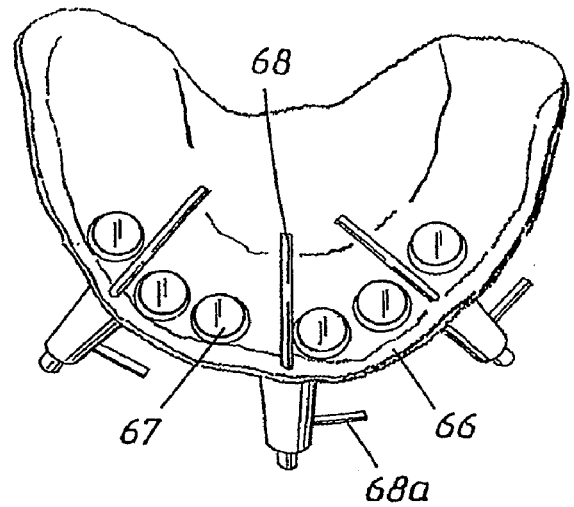
FIG. 6 shows a top view of the model according to FIG. 5.

A structural configuration of a physical template is indicated by 66 of FIG. 5 and FIG. 6. In the present embodiment, implants 67 are secured to the template in an assembled configuration. The anchoring pins are shown by 68. FIG. 6 shows the template according to FIG. 5 from underneath. The anchoring pins 68 are designed with manual actuating members configured to allow for screwing of the pins through the jaw bone. As shown, the anchoring pins may extend between the implants 67.

FIG. 7 shows, from the side and in perspective, the template according to FIGS. 5 and 6 applied to a jaw bone 69.

Although this disclosure has been described in terms of example embodiments and applications, other embodiments and applications apparent to those of ordinary skill in the art, including embodiments and applications that do not provide all of the benefits described herein, are also within the scope of this disclosure. The scope of the inventions is defined only by the claims, which are intended to be construed without reference to any definitions that may be explicitly or implicitly included in any of the incorporated-by-reference materials.

What is claimed is:

1. A method of constructing components related to a prosthetic installation, comprising:
   providing a template configured to be applied to the patient and to guide a drilling tool for drilling one or more holes in the patient's jawbone corresponding to the desired fixture locations; and
   creating a working model of the dental structure using the template.

2. The method of claim 1, comprising receiving the working model and constructing a prosthetic installation at least in part using the working model, the prosthetic installation configured to attach to the jawbone of the patient via one or more fixtures.

3. The method of claim 2, wherein the one or more fixtures are configured to be inserted in the one or more holes drilled in the patient's jawbone.

4. The method of claim 3, wherein the one or more holes drilled in the patient's jawbone are drilled through the template.

5. The method of claim 1, wherein creating the working model further comprises making an impression of the template.

6. The method of claim 1, wherein creating the working model further comprises constructing the working model from plaster.

7. The method of claim 1, further comprising generating a CAD file usable by a stereolithography machine for construction of the template.

8. The method of claim 7, further comprising receiving data corresponding to a graphical representation of a dental structure of a patient, the dental structure comprising at least a portion of the patient's jawbone.

9. The method of claim 8, further comprising receiving data corresponding to one or more desired fixture locations in the patient's jawbone, the desired fixture locations determined using, at least in part, the graphical representation of the dental structure of the patient.

10. The method of claim 1, further comprising forming the dental template using stereolithography technology.

11. The method of claim 1, further comprising mounting the working model to an articulator.

* * * * *